(12) United States Patent
Faltin et al.

(10) Patent No.: US 11,478,795 B2
(45) Date of Patent: Oct. 25, 2022

(54) MICROFLUIDIC DEVICE AND METHOD FOR ANALYZING NUCLEIC ACIDS

(71) Applicant: Robert Bosch GmbH, Stuttgart (DE)

(72) Inventors: Bernd Faltin, Gerlingen (DE); Jochen Rupp, Stuttgart (DE); Juergen Steigert, Stuttgart (DE); Christian Dorrer, Winnenden (DE); Karsten Seidl, Mülheim an der Ruhr (DE)

(73) Assignee: Robert Bosch GmbH, Stuttgart (DE)

( * ) Notice: Subject to any disclaimer, the term of this patent is extended or adjusted under 35 U.S.C. 154(b) by 665 days.

(21) Appl. No.: 16/348,264

(22) PCT Filed: Oct. 26, 2017

(86) PCT No.: PCT/EP2017/077448
§ 371 (c)(1),
(2) Date: May 8, 2019

(87) PCT Pub. No.: WO2018/086897
PCT Pub. Date: May 17, 2018

(65) Prior Publication Data
US 2019/0314818 A1    Oct. 17, 2019

(30) Foreign Application Priority Data
Nov. 10, 2016  (DE) ..................... 10 2016 222 032.2

(51) Int. Cl.
*C12Q 1/6806* (2018.01)
*B01L 3/00* (2006.01)

(52) U.S. Cl.
CPC ..... B01L 3/502753 (2013.01); B01L 3/50273 (2013.01); C12Q 1/6806 (2013.01); *B01L 2300/0681* (2013.01); *B01L 2300/088* (2013.01); *B01L 2300/0877* (2013.01); *B01L 2400/0475* (2013.01); *C12Q 2563/159* (2013.01)

(58) Field of Classification Search
CPC ............ C12Q 1/6806; C12Q 2563/159; B01L 3/502753; B01L 3/50273; B01L 2300/0681; B01L 2300/0877; B01L 2300/088; B01L 2400/0475
See application file for complete search history.

(56) References Cited

U.S. PATENT DOCUMENTS

| | | | |
|---|---|---|---|
| 2006/0013726 A1 | 1/2006 | Munenaka | |
| 2009/0325276 A1* | 12/2009 | Battrell | G01N 33/5302 435/287.2 |
| 2013/0040376 A1* | 2/2013 | Amshey | B01L 3/50273 435/287.2 |
| 2015/0232832 A1 | 8/2015 | Williams et al. | |
| 2015/0273470 A1* | 10/2015 | Hoffmann | B01L 3/5025 435/34 |
| 2017/0044483 A1* | 2/2017 | Faltin | C12N 1/06 |

FOREIGN PATENT DOCUMENTS

| | | |
|---|---|---|
| CN | 1973197 A | 5/2007 |
| CN | 101242901 A | 8/2008 |
| CN | 101415813 A | 4/2009 |
| CN | 103328981 A | 9/2013 |
| EP | 2 926 905 A1 | 10/2015 |
| JP | 2012-506995 A | 3/2012 |
| WO | 2005/011867 A2 | 2/2005 |
| WO | 2005/073691 A1 | 8/2005 |
| WO | 2006/076567 A2 | 7/2006 |
| WO | 2008/115626 A2 | 9/2008 |
| WO | 2010/025302 A2 | 3/2010 |
| WO | 2015/162059 A1 | 10/2015 |
| WO | 2016/205428 A1 | 12/2016 |

OTHER PUBLICATIONS

International Search Report corresponding to PCT Application No. PCT/EP2017/077448, dated Jan. 3, 2018 (German and English language document) (7 pages).

* cited by examiner

*Primary Examiner* — David C Thomas
(74) *Attorney, Agent, or Firm* — Maginot, Moore & Beck LLP

(57) ABSTRACT

A microfluidic device for analysing nucleic acids includes a pump unit with a pumping volume, a filter unit for receiving a lysate, and a reaction chamber. The pump unit, the filter unit and the reaction chamber are arranged in the stated order in a pump direction of the pump unit. The microfluidic device is configured to pump an elution medium via the pump unit into the filter unit for elution and subsequently into the reaction chamber for further treatment.

7 Claims, 1 Drawing Sheet

MICROFLUIDIC DEVICE AND METHOD FOR ANALYZING NUCLEIC ACIDS

This application is a 35 U.S.C. § 371 National Stage Application of PCT/EP2017/077448, filed on Oct. 26, 2017, which claims the benefit of priority to Serial No. DE 10 2016 222 032.2, filed on Nov. 10, 2016 in Germany, the disclosures of which are incorporated herein by reference in their entireties.

BACKGROUND

The disclosure relates to a microfluidic device and a method for analyzing nucleic acids.

Microfluidic devices are known for a very wide variety of purposes. However, known microfluidic devices have disadvantages for the analysis of nucleic acids, particularly relating to efficiency and accuracy of the analysis.

On the basis of this, a microfluidic device and a method according to the following description are described. Advantageous refinements and improvements of the microfluidic device and of the method are possible by the features mentioned in the following description.

SUMMARY

The term "microfluidic" relates here primarily to the size range of the microfluidic device. The microfluidic device is characterized in that physical phenomena, which are generally associated with microtechnology, are relevant in the fluid channels and chambers arranged therein. These include for example capillary effects, effects (in particular mechanical effects) which are related to surface tensions of the fluid. They furthermore include effects such as thermophoresis and electrophoresis. These phenomena are usually dominant in microfluidics over effects such as the force of gravity. The microfluidic device may also be characterized in that it is at least partially produced by a layerwise method and channels are arranged between layers of the layer structure. The term "microfluidic" may also be characterized by means of the cross sections inside the device, which are used for conveying the fluid. For example, cross sections in the range of from 100 μm [micrometers] times 100 μm to up to 800 μm times 800 μm are conventional.

The microfluidic device may, in particular, be a so-called "lab on a chip". Such a "lab on a chip" is intended and configured to carry out biochemical processes. This means that functionalities of a macroscopic laboratory are integrated, for example, into a plastic substrate. The microfluidic device may for example comprise channels, reaction chambers, prestored reagents, valves, pumps and/or actuation, detection and control units. The microfluidic device may make it possible to process biochemical processes fully automatically. In this way, for example, tests may be carried out on liquid samples. Such tests may, for example, be used in medicine. The microfluidic device may also be referred to as a microfluidic cartridge. In particular by introducing samples into the microfluidic device, biochemical processes may be carried out in the microfluidic device. In this case, additional substances, which initiate, accelerate and/or make possible the biochemical reactions may also be mixed with the samples.

The microfluidic device is preferably, in particular, configured and intended to analyze nucleic acids. This may, in particular, comprise analysis of DNA. The microfluidic device may in particular facilitate the conduct of a plurality, in particular even different analysis and detection methods.

The microfluidic device is preferably configured and intended to carry out analysis of nucleic acids as described below. If, for example, a sample to be analyzed comprises cells with DNA contained therein, the cells are initially disrupted. This is preferably done by lysis, i.e. by chemical, enzymatic and/or mechanical action (for example by means of ultrasound) on the cells. The result of such lysis is a lysate. The nucleic acids released from the cells during the lysis may subsequently be purified, processed further and/or analyzed. For example, the nucleic acids may be processed further by means of amplification. Amplification is intended, in particular, to mean the multiplication of DNA by an enzyme (for example polymerase). In particular, polymerase chain reaction (PCR) is preferred for the amplification. The term chain reaction in this case refers to the fact that a product of an amplification reaction may in turn be a starting substance for a new amplification reaction.

In order to purify the nucleic acids released from the cells, the lysate resulting from the lysis may have a binding buffer added to it and be brought in contact with a solid matrix. In particular, a filter is preferred as a solid matrix. Preferably, the nucleic acids are adsorbed on the filter.

Particularly for the adsorption of nucleic acids, the microfluidic device comprises the filter unit. The filter unit preferably comprises a filter which, as described, as a solid matrix is suitable for binding nucleic acids to itself. In this case, in particular, a silica filter is preferred because such a filter can bind nucleic acids to itself particularly well. Therefore, a silica filter is particularly suitable for use for the analysis of nucleic acids. The filter unit preferably comprises an inlet for the lysate, through which the lysate can be introduced into the filter unit and into the filter (particularly into the silica filter). The filter unit may preferably receive the lysate by the lysate being conveyed through the filter unit. In this case, the nucleic acids may be bound to the filter.

The application of the lysate to the filter unit is preferably carried out with the aid of the pump unit which delivers the lysate into the filter.

After the nucleic acids from the lysate have been bound to the filter (particularly inside the filter unit), a further purification and/or washing process may optionally be carried out. Subsequently, the nucleic acids may be eluted, i.e. extracted from the filter. To this end, the filter is preferably flushed through with an elution medium. The elution medium is preferably water, water to which Tween has been added, or an elution buffer.

The elution medium is preferably provided in a storage container. The storage container is preferably contained in the microfluidic device. In particular, it is preferred for the microfluidic device to comprise a storage container which contains precisely the amount of elution medium which is required for an analysis process by means of the microfluidic device. A plurality of such storage containers may also be provided, in order to be able to correspondingly carry out a plurality of analysis processes with the microfluidic device (e.g. before refilling of the storage containers is required). As an alternative, the elution medium may also be introduced into the microfluidic device from outside the microfluidic device through an inlet.

The elution medium is preferably pumped through the pump unit into the filter unit. To this end, the pump unit is preferably connected to the storage container, or to the inlet of the microfluidic device for the elution medium, as well as to the filter unit through connecting lines. The connecting lines may, in particular, be components such as tubes and channels of a microfluidic network.

The pump unit is preferably intended and configured in order to deliver a fluid (in particular a liquid) through a line. The pump unit may be driven mechanically, electrically or pneumatically. For example, the pump unit may comprise a pump space with a variable volume, which can be emptied by manual compression (for example by hand). By such emptying, the liquid contained in the pump unit, or in the pump space of the pump unit, may be delivered from the pump unit. In particular, it is preferred for the pump unit to comprise a micromembrane pump.

The pump volume defines how much of a fluid can be received inside the pump unit for an equal time for the pumping. In the case of a cyclically operable pump, the pump volume corresponds to the amount of fluid which can be delivered by one pump cycle. A pump cycle of a cyclically operating pump is intended to mean that the pump unit is filled with the fluid and subsequently emptied again.

Preferably, the pump unit comprises an inlet and an outlet for the fluid. The pump unit may, for example, continuously aspirate the fluid at the inlet and eject it at the outlet. In the case of a cyclically operating pump unit, a pump cycle may be defined in that the fluid is first aspirated through the inlet and subsequently (after the pump unit has been filled) delivered from the outlet. The pump direction of the pump unit is directed from the inlet to the outlet. The inlet of the pump unit is preferably connected to the storage container, or to the inlet of the microfluidic device for the elution medium. The outlet of the pump unit is preferably connected to the filter unit.

In one preferred embodiment variant, the storage container may also be replaceable. The storage container may also comprise a multiplicity of (at least two) container chambers in which different media are provided. The term "different media" comprises in this case particularly lysates, elution media and optionally binding buffer (or also washing buffer). Valves or the like may also preferably be arranged in a channel which fluidically connects the storage container, or the container chambers, to the pump unit, in order to control a fluidic connection between the storage container, or the container chambers, and the pump unit. Optionally, connections by which media (in particular lysates, elution media, binding buffer) can be provided to the device, can also be provided upstream (i.e. on the storage container side) of the pump unit.

The elution medium driven by the pump unit may preferably flow through the filter unit in such a way that the elution medium extracts the nucleic acids bound in the filter unit (in particular on the silica filter) from the filter and takes them up (i.e. it elutes the nucleic acids). After the elution, the elution medium, which then also contains the nucleic acids, is referred to as an eluate. It is in particular preferred for the elution medium, or the eluate, to comprise the nucleic acids to be analyzed, after leaving the filter unit. The filter unit preferably comprises an inlet and an outlet for the elution medium, or for the eluate. Preferably, the inlet and the outlet of the filter unit for the elution medium, or for the eluate, are different to the inlet of the filter unit described above for the lysate. As an alternative, the lysate may also be introduced into the filter unit through the inlet and/or through the outlet of the filter unit for the elution medium, or for the eluate.

The elution medium, or the eluate, may (including the nucleic acids which it comprises) be processed further after emerging from the filter unit. In particular enzymatic reactions, for example amplification (in particular PCR), sequencing and restriction enzyme digestion, are preferred as further processes.

In order to carry out PCR after purification, for example, the eluate or a portion of the eluate is preferably mixed with reagents, for example a PCR reaction mixture, and subsequently thermally cycled. The PCR reaction mixture may for example contain oligonucleotides, primers, salts and/or the enzyme polymerase.

The reaction chamber is preferably used for mixing with reagents and/or carrying out an in particular enzymatic reaction. The reaction chamber is preferably connected by means of a connecting line to the filter unit (in particular to the outlet of the filter unit for the elution medium, or for the eluate). Preferably, the reagents are prestored in the reaction chamber, particularly in freeze-dried or lyophilized form. By the admission of the eluate, the reagents prestored in this way are dissolved during the admission of the eluate.

Preferably, the filter unit and the reaction chamber (and in particular the volumes of the filter unit and of the reaction chamber) are adapted to one another in such a way that an eluate volume which can be obtained from the filter unit can be introduced fully into the reaction chamber, the reaction chamber preferably being fully filled. This thus means that neither an excess of the eluate volume remains, nor is the eluate volume smaller than the volume of the reaction chamber. In particular, it is preferred for no gas bubbles to be formed in the reaction chamber during the introduction of the eluate into the reaction chamber. Furthermore, the storage container, or the storage container chambers, (and in particular the volume thereof) is preferably adapted to the filter unit and to the reaction chamber (and in particular to the volumes of the filter unit and of the reaction chamber) in such a way that a volume of the elution medium released from the storage container corresponds to the volume of eluate which can exactly fill the reaction chamber. In this case, it may optionally be taken into account that the eluate may be mixed with reagents before entry into the reaction chamber or in the reaction chamber. A volume of the reagents is preferably taken into account in such a way that the volume of the storage container is smaller by the volume of the reagents than the volume of the reaction chamber. It is furthermore preferred for the pump unit to comprise a cyclically operating pump. In this way, the pumped volume of elution medium can be controlled particularly well. It is particularly preferred for the pump volume of the cyclically operating pump to correspond precisely to the required amount of elution medium (i.e. the pump volume is in particular identical to the volume of the filter unit), so that a single pump cycle is sufficient in order to fill the filter unit.

If the filter unit and the reaction chamber (and optionally also the storage container) are adapted to one another as described, the eluate may be used fully for further processing steps (for example PCR). In this way, all the eluted nucleic acids can be used for the further processing. This leads to a sensitivity increase of the analysis. In the case of such full utilization of the eluate, the further analysis can also be carried out particularly rapidly. For example, in the case of a large starting amount of eluate, and/or in the case of a large starting number of nucleic acid molecules, repeated amplification may be obviated and only one amplification cycle may be carried out. This means that a smaller number of amplification cycles can yield the same amount of product by increasing the starting amount (or by full use of the eluate).

Furthermore, the microfluidic device preferably comprises valves controlling the flow of the elution medium, or of the eluate.

In one preferred embodiment of the microfluidic device, a volume of the reaction chamber is at most 20% greater than the pump volume.

In this embodiment, it is preferred for the pump unit to comprise a cyclically operating pump. The pump unit, and in particular the pump volume, are preferably adapted to the filter unit and to the reaction chamber (and optionally also to the storage container), or to the respective volumes. Preferably, all of the elution medium contained in the storage container can be introduced into the pump volume, the pump volume being fully filled. By the cyclical mode of operation of the pump, the pump volume can be fully filled. Subsequently, the elution medium is preferably pumped into the filter unit. It is preferred that all of the elution medium can be introduced from the pump unit into the filter unit, the filter unit being fully filled. Furthermore, the elution medium (which then contains the nucleic acids and is in the form of an eluate) may be conveyed from the filter unit into the reaction chamber. In this case, it is preferred that the eluate can be introduced fully into the reaction chamber, and that the reaction chamber can be fully filled. If mixing with reagents is not provided, it is preferred for the volumes of the storage container, of the pump (i.e. the pump volume), of the filter unit and of the reaction chamber respectively to be equally large. If mixing of the eluate with reagents is provided during entry into the reaction chamber or between outlet from the filter unit and inlet into the reaction chamber, the volume of the reaction chamber is preferably smaller by the volume of the reagents than the respective volumes of the storage container, of the pump (i.e. the pump volume) and of the filter unit.

In particular, it is therefore preferred for the volume of the reaction chamber to be at most 20% greater than the pump volume. This means that the volume of reagents which is to be taken into account corresponds at most to the 20% volume difference between the reaction chamber and the pump unit (or the pump volume). It is particularly preferred for the pump volume to be from 20 to 30 µl [microliters] and for the volume of the reaction chamber to be from 20 to 35 µl (so far as the above condition is complied with that the volume of the reaction chamber is at most 20% greater than the pump volume).

In another preferred embodiment, the microfluidic device furthermore comprises a first side channel for diverting a content of the pump unit downstream of the pump unit.

The first side channel preferably branches off downstream of the pump unit, i.e. after the pump unit in the pump direction, in particular between the pump unit and the filter unit. The first side channel preferably comprises a valve, in order to open the first side channel only optionally. In particular, it is preferred for the first side channel to be opened while the pump unit is being filled. In this case, the pump unit may be fully filled, in which case excess elution medium may flow away through the first side channel (instead of entering the filter unit before this is desired). After the pump unit is fully filled, the first side channel is preferably closed (by means of the valve in the first side channel). The elution medium may then be pumped from the pump unit past the first side channel into the filter unit. The first side channel may lead into the surroundings of the microfluidic device (and for example into a collection container there). The first side channel may also lead into a collection container or into other regions (for example into channels) inside the microfluidic device. It is preferred for the first side channel to lead (back) into the storage container so that elution medium conveyed through the first side channel can be reused.

In another preferred embodiment, the microfluidic device furthermore comprises a second side channel for diverting a content of the filter unit downstream of the filter unit.

The second side channel preferably branches off downstream of the filter unit, i.e. after the filter unit in the pump direction, in particular between the filter unit and the reaction chamber. The second side channel preferably comprises a valve, in order to open the second side channel only optionally. In particular, it is preferred for the second side channel to be opened while the filter unit is being filled. This may permit prefilling of the filter unit (and in particular of the silica filter) with elution medium before the elution is carried out. The prefilling may also be carried out with a washing buffer and/or a binding buffer. Furthermore, contamination or residues of a washing buffer may be washed from the filter unit before the elution is carried out. The filter unit may preferably be fully filled, in which case excess elution medium (or excess washing buffer and/or binding buffer) may flow away through the second side channel (instead of entering the reaction chamber before this is desired). After the filter unit is fully filled, the second side channel is preferably closed (by means of the valve in the second side channel). The elution medium may then be pumped from the pump unit past the second side channel into the reaction chamber. The second side channel may lead into the surroundings of the microfluidic device (and for example into a collection container there). The second side channel may also lead into a collection container or into other regions (for example into channels) inside the microfluidic device.

In another preferred embodiment, the microfluidic device furthermore comprises a return line arranged parallel to the filter unit.

The return line preferably branches off downstream of the filter unit, in particular between the filter unit and the reaction chamber. The elution medium may be taken from there (in particular from a connecting line between the filter unit and the reaction chamber) and fed back through the return line. In particular, the return may be carried out in such a way that the elution medium taken can be added back at a position upstream of the filter unit. To this end, the return line is preferably connected to a connecting line between the pump unit and the filter unit (or also to an outlet of the pump unit or to an inlet of the filter unit). The return line preferably comprises an additional return pump. As an alternative, the elution medium may preferably be pumped through the return line because of a pressure generated by the pump unit. In particular, it is preferred for the return line to be formed together with the first side channel and/or with the second side channel. This may, for example, mean that the return line is formed as a connecting line between the first side channel and the second side channel. The return line may also, for example, branch off at a position between the filter unit and the reaction chamber, which position is different to a branching position of the second side channel, and subsequently open into the first side channel. The return line may also branch off from the second side channel and open at a position into a connecting line between the pump unit and the filter unit, which position is different to a branching position of the first side channel.

By means of the return line, the elution medium can be conveyed repeatedly through the filter unit. In this case, nucleic acids bound in the filter unit can be extracted and taken up by the elution medium (i.e. eluted) particularly well.

In another preferred embodiment, the microfluidic device furthermore comprises a mixing chamber, which is connected to the filter unit and/or to the reaction chamber.

Preferably, the eluate can be introduced from the filter unit selectively into the reaction chamber and/or into the mixing chamber. In particular, it is preferred that reagents required for a reaction in the reaction chamber are prestored in the mixing chamber. Mixing of the reagents with the eluate and/or dissolving of the reagents (if they are prestored in freeze-dried form, for example) may be carried out in the mixing chamber. By means of the mixing chamber, spatial separation of the mixing of the reagents with the eluate and/or of the dissolving of the reagents from the conduct of the reaction is possible. In this way, it is possible to achieve the effect that the reaction chamber is fully filled, in particular while avoiding gas bubbles. Without such spatial separation, gas inclusions could be formed inside the reaction chamber by the mixing of the reagents with the eluate and/or by the dissolving of the reagents. Such gas bubbles could detrimentally influence the reaction to be carried out.

By spatial separation of the mixing chamber and reaction chamber, particularly rapid and particularly well-defined introduction of the eluate into the mixing chamber may also be carried out. In this way, particularly good dissolving of the reagents can be achieved. In particular, the formation of gas bubbles can be suppressed particularly well in this case.

The mixing chamber preferably has a volume which corresponds to the pump volume.

Preferably, the mixing chamber may also be used as a pump chamber, so that the elution medium (to which dissolved reagents are then optionally added) can preferably be pumped out from the mixing chamber and into the reaction chamber. The mixing chamber is in this case preferably configured as a pump chamber. This means that, for example, reagents may be prestored in a mixing chamber configured as a pump chamber. After the filling of the mixing chamber, in particular with the eluate, a membrane of the mixing chamber may be deflected and the mixture may thus be displaced from the mixing chamber into the reaction chamber.

The eluate may also initially be mixed with the reagents in the mixing chamber, pumped into the reaction chamber and subsequently pumped back into the mixing chamber for further processing.

Two elution processes may also be carried out successively, for example one in the second side channel and one in the reaction chamber. The two eluate fractions (i.e. the fractions of the eluate which are processed separately from one another) may subsequently be mixed. This may have the advantage that contamination possibly contained in a first of the eluate fractions can be diluted.

As another aspect, a method for analyzing nucleic acids as disclosed herein is proposed.

The abovedescribed advantages and configuration features of the microfluidic device may be applied and adapted to the described method, and vice versa.

The method steps indicated are preferably, but not necessarily, carried out in the order indicated.

In step b), the lysate of the sample, which is provided in step a), is preferably introduced into the filter unit. The filter material is preferably located inside the filter unit. The filter material may, in particular, be in the form of a silica filter. In step c), pumping of the elution medium is carried out preferably by means of the pump unit. By the abovedescribed preferably mutually adapted volumes of the components of the microfluidic device, step d) may be carried out by utilizing all of the elution medium (or eluate) used in step c).

In one preferred embodiment, the method furthermore comprises the method step:

e) dissolving of prestored reagents by the elution medium.

Reagents dissolved in step e) may, for example, be PCR reagents. The reagents are preferably prestored in the reaction chamber and/or in the mixing chamber, particularly in freeze-dried form.

In another preferred embodiment of the method, the microfluidic device is at least temporarily oriented in such a way that the reaction chamber is arranged above the filter unit.

Preferably, the microfluidic device is oriented as described throughout the duration of the method. That the reaction chamber is arranged above the filter unit is to be understood in relation to terrestrial gravitation. This means that, in an orientation of the microfluidic device in which the reaction chamber is arranged above the filter unit, the terrestrial gravitation acts for example on the elution medium in a direction from the reaction chamber to the filter unit. In this way, the formation of gas bubbles inside the reaction chamber can be suppressed particularly well.

Even in the case of perfect filling of a chamber, gas bubbles may be formed during the dissolving of lyophilized reagents. In this method, these gather on an upper side of the chamber in which the reagents are dissolved. Preferably, for this embodiment of the method, a microfluidic device having a mixing chamber and a reaction chamber is used. In this case, it is preferred for a connecting line between the mixing chamber and the reaction chamber to have a line volume which corresponds to an (expected) volume of the gas bubbles formed. In this way, during the transfer of the eluate from the mixing chamber into the reaction chamber, the gas formed can collect in the connecting line while the eluate can be pumped without gas inclusions into the reaction chamber.

BRIEF DESCRIPTION OF THE DRAWINGS

The disclosure and the technical field will be explained in more detail below with the aid of the figures. The figures show particularly preferred exemplary embodiments, although the disclosure is not restricted to these. In particular, it is to be pointed out that the figures, and in particular the size proportions represented, are only schematic. Schematically.

DETAILED DESCRIPTION

Figure 1:
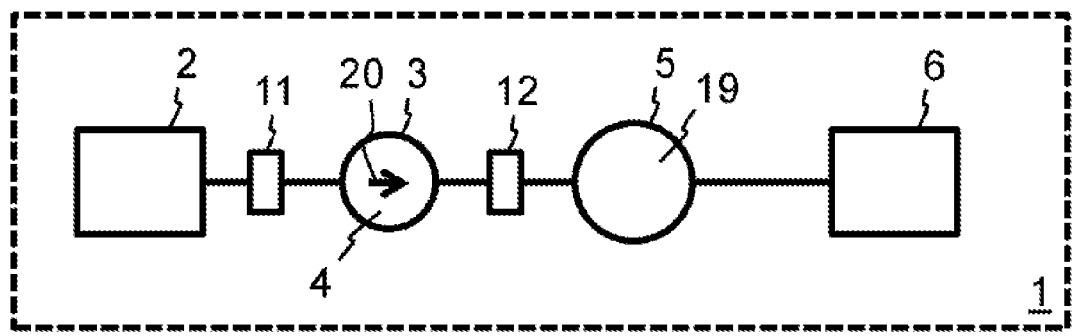
FIG. 1 shows a microfluidic device for analyzing nucleic acids in a first embodiment.

FIG. 1 shows a first embodiment of a microfluidic device 1 for analyzing nucleic acids. The microfluidic device 1 comprises a storage container 2, a pump unit 3 having a pump direction 20, a filter unit 5 for receiving a lysate and a reaction chamber 6, which are arranged in the order indicated in a pump direction of the pump unit 3. In the representation of FIG. 1, the pump unit points from left to right, which is indicated by an arrow in the pump unit 3. The filter unit 5 comprises a filter material 19. The pump unit 3 has a pump volume 4. The microfluidic device 1 is configured in order to pump an elution medium from the storage container 2 through the pump unit 3 for elution into the filter unit 5 and subsequently to pump it for further processing into the reaction chamber 6. Furthermore indicated are a first valve 11 and a second valve 12.

Figure 2:
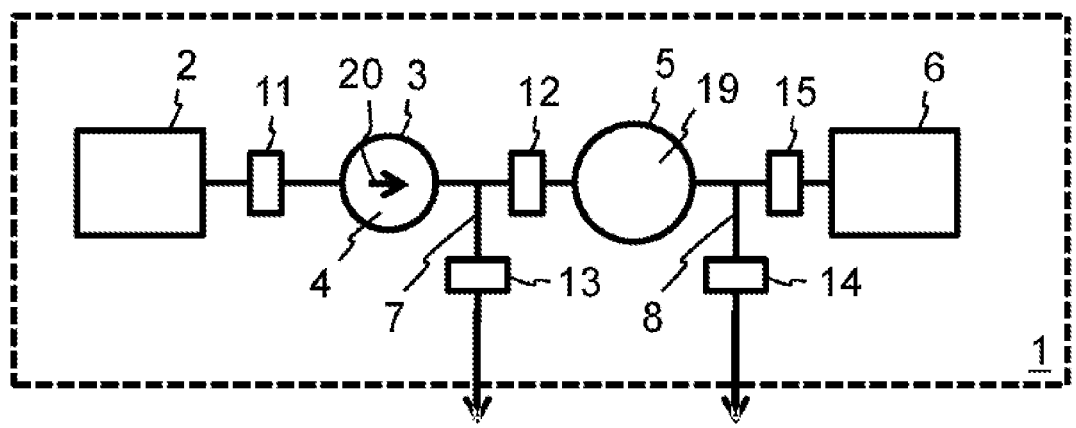
FIG. 2 shows a microfluidic device for analyzing nucleic acids in a second embodiment.

FIG. 2 shows a second embodiment of a microfluidic device 1, which represents a development of the first embodiment. The elements not described below are identical to those from the first embodiment. Compared with the first embodiment, the second embodiment additionally comprises a first side channel 7, which branches off between the pump unit 3 and the first valve 11 from a connecting line between the pump unit 3 and the filter unit 5. The first side channel 7 comprises a third valve 13. The first side channel 7 leads out of the microfluidic device 1, which is indicated by an arrow. Compared with the first embodiment, the second embodiment furthermore additionally comprises a second side channel 8, which branches off between the filter unit 5 and a fifth valve 15 from a connecting line between the filter unit 5 and the reaction chamber 6. The second side channel 8 comprises a fourth valve 14. The second side channel 8 leads out of the microfluidic device 1, which is indicated by an arrow.

Figure 3:
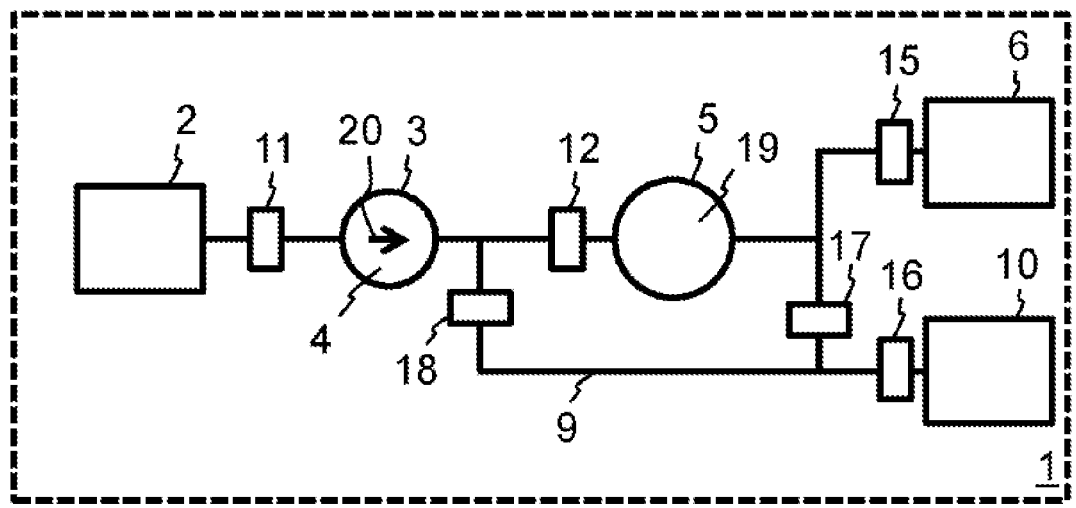
FIG. 3 shows a microfluidic device for analyzing nucleic acids in a third embodiment.

FIG. 3 shows a third embodiment of a microfluidic device 1, which represents a development of the first embodiment. The elements not described below are identical to those from the first embodiment. Besides the reaction chamber 6, the microfluidic device 1 comprises a mixing chamber 10. The mixing chamber 10 may be used in order to mix an elution medium with reagents in a manner spatially separated from the reaction chamber 6. While the reaction chamber 6 is connected to the filter unit 5 by means of the fifth valve 15, the mixing chamber 10 is connected to the filter unit 5 by means of a sixth valve 16 and a seventh valve 17. At a position between the sixth valve 16 and the seventh valve 17, a return line 9 branches off, which return line opens at a position between the pump unit 3 and the second valve 12 into a connecting line between the pump unit 3 and the filter unit 5. The return line 9 is arranged parallel to the filter unit 5 and makes it possible to convey an elution medium repeatedly through the filter unit. The return line comprises an eighth valve 18.

The invention claimed is:

1. A microfluidic device for analyzing nucleic acids, comprising:
   a pump unit having a pump volume and an outlet;
   a filter unit configured to receive a lysate;
   a first channel configurable to fluidically connect the outlet to the filter;
   a second channel in fluid communication with the first channel at a location between the outlet and the filter unit;
   a reaction chamber; and
   a third channel configurable to fluidically connect the filter unit to the reaction chamber, wherein:
   the pump unit, the filter unit and the reaction chamber are arranged in the order specified in a pump direction of the pump unit, and
   the microfluidic device is configurable to pump at least a portion of an elution medium through the pump unit for elution into the filter unit and subsequently to pump the elution medium for further processing into the reaction chamber.

2. The microfluidic device as claimed in claim 1, wherein a volume of the reaction chamber is at most 20% greater than the pump volume.

3. The microfluidic device as claimed in claim 1, further comprising:
   a fourth channel in fluid communication with the second channel at a location between the filter unit and the reaction chamber.

4. The microfluidic device as claimed in claim 3, further comprising:
   a return line configurable to fluidically connect the second channel and the third channel.

5. The microfluidic device as claimed in claim 1, further comprising a mixing chamber configurable to be fluidically connected to the filter unit and/or to the reaction chamber.

6. The microfluidic device as claimed in claim 1, further comprising:
   a chamber in fluid communication with the second channel.

7. The microfluidic device as claimed in claim 1, further comprising:
   a container in fluid communication with the second channel.

* * * * *